(12) United States Patent
Casal et al.

(10) Patent No.: US 6,281,005 B1
(45) Date of Patent: Aug. 28, 2001

(54) AUTOMATED NUCLEIC ACID COMPACTION DEVICE

(75) Inventors: Hector L. Casal, Shaker Heights; Mark J. Cooper, Solon; Tomasz H. Kowalczyk, University Heights; Murali Krishna Pasumarthy, Willoughby Hills, all of OH (US); Jose C. Perales, Barcelona (ES); Steven J. Torontali, Moreland Hills, OH (US)

(73) Assignee: Copernicus Therapeutics, Inc., Cleveland, OH (US)

( * ) Notice: Subject to any disclaimer, the term of this patent is extended or adjusted under 35 U.S.C. 154(b) by 0 days.

(21) Appl. No.: 09/311,553

(22) Filed: May 14, 1999

(51) Int. Cl.[7] ............................. C12M 1/34; C12Q 1/68; C07H 19/00; A61K 48/00; G01N 15/02

(52) U.S. Cl. .................... 435/287.2; 435/6; 435/7.1; 435/286.7; 435/287.7; 435/288.7; 435/291.5; 702/22; 702/25; 536/22.1; 536/23.1; 366/197; 366/241; 366/279; 356/335; 356/336; 356/337; 356/338; 574/44

(58) Field of Search ..................... 435/5, 6, 7.1, 283.1, 435/285.1, 286.1, 286.2, 286.3, 286.4, 286.5, 286.6, 286.7, 287.2, 287.1, 287.3, 288.1, 288.4, 288.5, 288.7, 289.1, 291.6, 291.5, 291.7, 298.1; 702/22, 25; 536/22.1, 23.1; 366/279, 241, 197; 356/335–338, 300; 436/43, 86; 514/44

(56) References Cited

U.S. PATENT DOCUMENTS

| 3,780,992 | 12/1973 | Nishi et al. . |
|---|---|---|
| 4,046,515 | 9/1977 | de Leeuw . |
| 4,341,736 | 7/1982 | Drbal et al. . |
| 4,612,291 | 9/1986 | Dawes . |
| 4,911,556 | * 3/1990 | Lim et al. ........................ 366/279 |
| 4,927,062 | 5/1990 | Walsh . |
| 4,930,898 | 6/1990 | Miller-Ihli . |
| 5,122,342 | 6/1992 | McCulloch et al. . |
| 5,240,842 | 8/1993 | Mets . |
| 5,354,844 | 10/1994 | Beug et al. . |
| 5,365,798 | 11/1994 | Kressirer . |

(List continued on next page.)

OTHER PUBLICATIONS

Ibañez, Miguel et al. "Spermidine–condensed DNA and cone–shaped lipids improve delivery and expression of exogenous DNA transfer by liposomes" Biochem Cell Biol. vol. 74 1996, pp. 633–643.

Lee, Robert J. et al. "Folate–targeted, Anionic Liposome–entrapped Polylysine–condensed DNA for Tumor Cell–specific Gene Transfer" The Journal of Biological Chemistry vol. 271, No. 14, 1996, pp. 8481–8487.

Primary Examiner—Kenneth R. Horlick
Assistant Examiner—Jeffrey Siew
(74) Attorney, Agent, or Firm—BB Banner&Witcoff, Ltd.

(57) ABSTRACT

An automated nucleic acid compaction device for analyzing and compacting a nucleic acid complex into unimolecular nucleic acid particles. Broadly, the device includes a container support and agitation system; a measuring and testing system; and a dispensing system; all controlled by a control system. The control system controls the support and agitation system and the dispensing system based either on a predetermined formulation or by analysis of feedback data provided by the measuring and testing system. In a preferred embodiment, the device is a real-time measuring and mixing instrument operating in a closed loop system. The preferred embodiment also comprises a monitoring system including a submersible probe which is positioned in the batch solution to provide data to a controller. Once a desired level of nucleic acid compaction is reached, as detected by the monitoring system, the controller stops the dispensing and mixing agitating systems.

59 Claims, 12 Drawing Sheets

U.S. PATENT DOCUMENTS

| | | |
|---|---|---|
| 5,480,772 | 1/1996 | Wangh . |
| 5,521,291 | 5/1996 | Curiel et al. . |
| 5,544,535 | 8/1996 | Thomas . |
| 5,612,205 | 3/1997 | Kay et al. . |
| 5,614,503 | 3/1997 | Chaudhary et al. . |
| 5,626,561 | 5/1997 | Butler et al. . |
| 5,641,680 | 6/1997 | Zhao . |
| 5,651,981 | 7/1997 | Ashley et al. . |
| 5,661,018 | 8/1997 | Ashley et al. . |
| 5,661,025 | 8/1997 | Szoka, Jr. et al. . |
| 5,679,559 | 10/1997 | Kim et al. . |
| 5,679,575 * | 10/1997 | Kubota et al. .......................... 436/49 |
| 5,877,302 | 3/1999 | Hanson et al. . |
| 6,052,184 * | 4/2000 | Reed .................................. 356/338 |

* cited by examiner

EXPERIMENT 140

AUTOMATED NUCLEIC ACID COMPACTION DEVICE

FIELD OF THE INVENTION

The present invention relates to a device which produces compacted nucleic acid in a reproducible, pharmaceutical context for use in gene therapy studies and treatments, and more particularly unimolecular DNA.

BACKGROUND OF THE INVENTION

Genetic engineering broadly, and gene therapy studies, in particular, involve the genetic transformation of living host cells by introduction of exogenous materials such as foreign DNA to the host cells to change or modulate the host cells. When successful, the genes carried by the foreign DNA are expressed in the host cells, and thus, the host cells are transformed. Genetically transformed cells or tissues are of great value in research, medicine and agriculture.

There are several conventional gene transfer techniques which are routinely used such as cell fusion, electroporation, liposome fusion, calcium phosphate precipitation, viral infection, conjugal transfer, micropipette microinjection and aerosol beam microinjection. While much research is dedicated to gene transfer techniques, all of these conventional transfer technologies deal with DNA, DNA/liposome or DNA/protein particles in large, noncondensed forms. Noncondensed DNA particles are less stable since there are nucleases in blood which can destroy noncondensed DNA, and noncondensed DNA particles are likely too large to fit into a cellular endosome following receptor-mediated endocytosis, or to be transported into the nucleus of postmitotic cells. Therefore, the effective transfer of genes remains an obstacle in many fields of research.

It has been recognized that DNA particles in condensed form are more effective in successfully delivering the DNA payload to target tissues while remaining stable and permitting receptor-mediated endocytosis. With this recognition, the literature teaches adding DNA and condensing proteins together while mixing, generally at low concentrations of each. This produces condensed DNA particles called $\psi$-form DNA which consists of approximately 10–50 molecules of DNA and many molecules of condensing proteins. A laboratory method for the production of $\psi$-DNA is described in Perales, et al., Biochemical and Functional Characterization of DNA Complexes Capable of Targeting Genes to Hepatocytes via the Asialoglycoprotein Receptor, J. of Biological Chemistry, vol. 272, pp.7398–7407, which is herein incorporated by reference. These $\psi$-DNA particles have a size on the order of 100 to 200 nm which are improved over noncondensed particles, but do not completely eliminate the stability, efficiency and specificity problems of the larger particles altogether.

Condensation of DNA particles to smaller sizes than $\psi$-DNA has been heretofore achieved manually by highly trained individuals in a lab. A preferred form of DNA particles which are condensed even smaller than the $\psi$-DNA is unimolecular, which refers to DNA complexes which consist of a single unit of DNA plasmid; these particles are referred to as compacted DNA particles to distinguish them from condensed DNA particles which consist more typically of multiple molecules of DNA. Due to the multiple steps of such a manual procedure and the number of variables inherent in the operation, the successful production of compacted DNA particles is more akin to an art form practiced by a few qualified individuals rather than a repeatable pharmaceutical production method. These unimolecular formulations of compacted DNA are stable, and, compared to other formulations, more effectively transfer DNA to the nucleus of target tissues following intravenous and other routes of administration.

One of the limitations of conventional gene transfer techniques has been the size of DNA particles which are introduced to target tissues. The instability of large DNA particles and the unsatisfactory level of gene transfer with conventional condensed DNA particles have prompted the use of smaller, compacted forms of DNA particles. A discussion of compacted nucleic acids and their delivery to cells as well as the advantages of using compacted DNA is disclosed in commonly assigned U.S. Pat. Nos. 5,844,107 and 5,877,302, the entire disclosures of which are hereby incorporated by reference. Since the production of compacted DNA manually is expensive, time-consuming and sometimes inconsistent, there is a need for an automated device which produces compacted, unimolecular DNA particles in a controlled, pharmaceutical production method.

SUMMARY OF THE INVENTION

Accordingly, it is a principal object of the present invention to provide an automated DNA compaction device which produces unimolecularly compacted DNA particles in an unaggregated formulation.

Another object of the present invention is to provide a series of automated steps to produce compacted DNA particles consistently and repeatedly A further object of the invention is to provide a control system for an automated DNA compaction device.

Directed to achieving these objects, an automated nucleic acid compaction device is provided which is a real-time measuring and mixing instrument operating as a closed loop system in either automatic or manual mode. Broadly, the device includes the following components: a support and agitation system; a measuring and testing system; and a dispensing system; all controlled by a control system. The control system controls the support and agitation system and the dispensing system based either on a predetermined formulation or by analysis of feedback data provided by the measuring and testing system. Once a desired level of nucleic acid compaction is reached, the control system ensures that dispensing and agitation, if applicable, are ceased so that the compacted nucleic acid can be removed from the device.

In a preferred embodiment, the support and agitation system of the compaction device comprises a vortexing device such as a magnetic stirring table for supporting a beaker of a nucleic acid solution into which mixing solutions are dispensed during the compaction process. The nucleic acid and mixing solutions are disclosed in U.S. Pat. Nos. 5,844,107 and 5,877,302. It is to be understood that the nucleic acid may be a DNA, RNA, or a DNA or RNA derivative such as a derivative resistant to degradation in vivo as discussed in the patents.

The measuring and testing system of the compaction device comprises a probe disposed in the beaker of initial batch solution and a monitoring device coupled to the control system for iterative feedback of readings to the control system.

The dispensing system of the compaction device comprises pumps and stepper motors to operate micro-liter syringes which dispense additive solutions into the beaker. The dispensing system also comprises a dispersion system in the form of a sonication device to disperse the additive solutions. The control system commands the dispensing system.

The control system of the compaction device comprises a CPU and operational software which receives readings from the measuring and testing system, analyzes the data and compares the data to initial readings and desired readings, and signals the dispensing system to dispense additive solution to the batch solution if necessary. In this manner, precise control over the additive solution is maintained by the control system.

These and other features and advantages of the invention may be more completely understood from the following detailed description of the preferred embodiments of the invention with reference to the accompanying drawings.

DETAILED DESCRIPTION OF PREFERRED EMBODIMENTS

Broadly, an automated DNA compaction device comprises components which support and mix or agitate a batch solution of compaction reagents to which particular additive solutions are added until compaction of DNA is obtained to a desired level. In one preferred embodiment, the initial batch solution comprises DNA and the additive solution comprises one or more polycations. In another preferred embodiment, the initial batch solution comprises one or more polycations and the additive solution comprises DNA. For a particular compacted DNA complex, the amounts of batch solution and additive solutions, and the rate at which the additive solutions are admixed, can be formulated to obtain a desired end amount of compacted DNA in a desired size or form. Once such a formulation is developed, it is contemplated that the automated DNA compaction device, or a larger scale device, can be provided with the necessary solutions to produce any amount of compacted DNA in a manufacturing setting.

In order to develop such a formulation, an automated DNA compaction device like the device set forth as a preferred embodiment would be used. A preferred embodiment disclosed herein includes components coupled to a control system which operates the components in an iterative, closed loop system with a feedback loop that communicates the state of the nucleic acid complex composition. Of course a feedback loop may not be necessary if a predetermined formulation of solutions and addition rates were used.

While the preferred embodiments pertain to a particular scale of production, the present invention is contemplated to be configurable for any scale of production and predetermined formulations.

Figure 1:
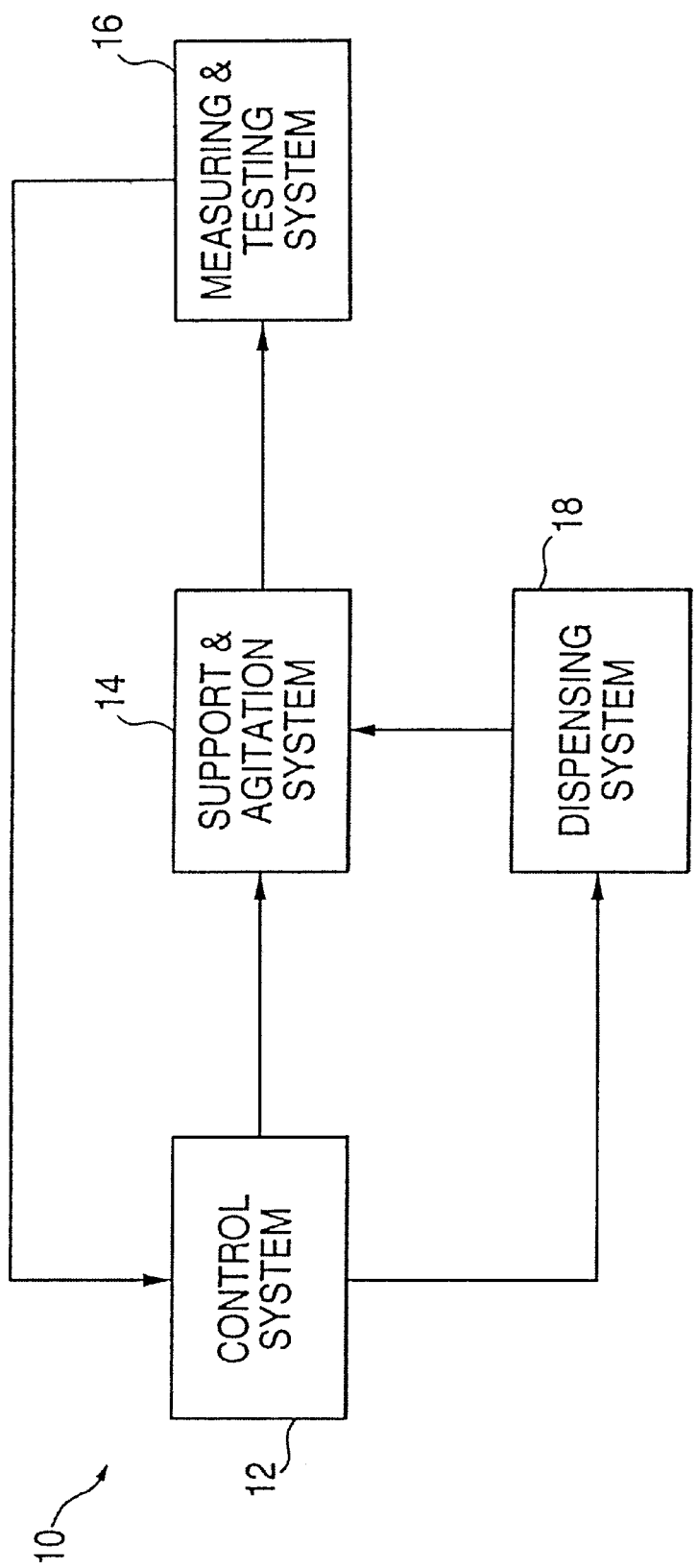
FIG. 1 is a block diagram of the closed loop systems of the automated DNA compaction device in accordance with a preferred embodiment of the present invention.
Figure 2:
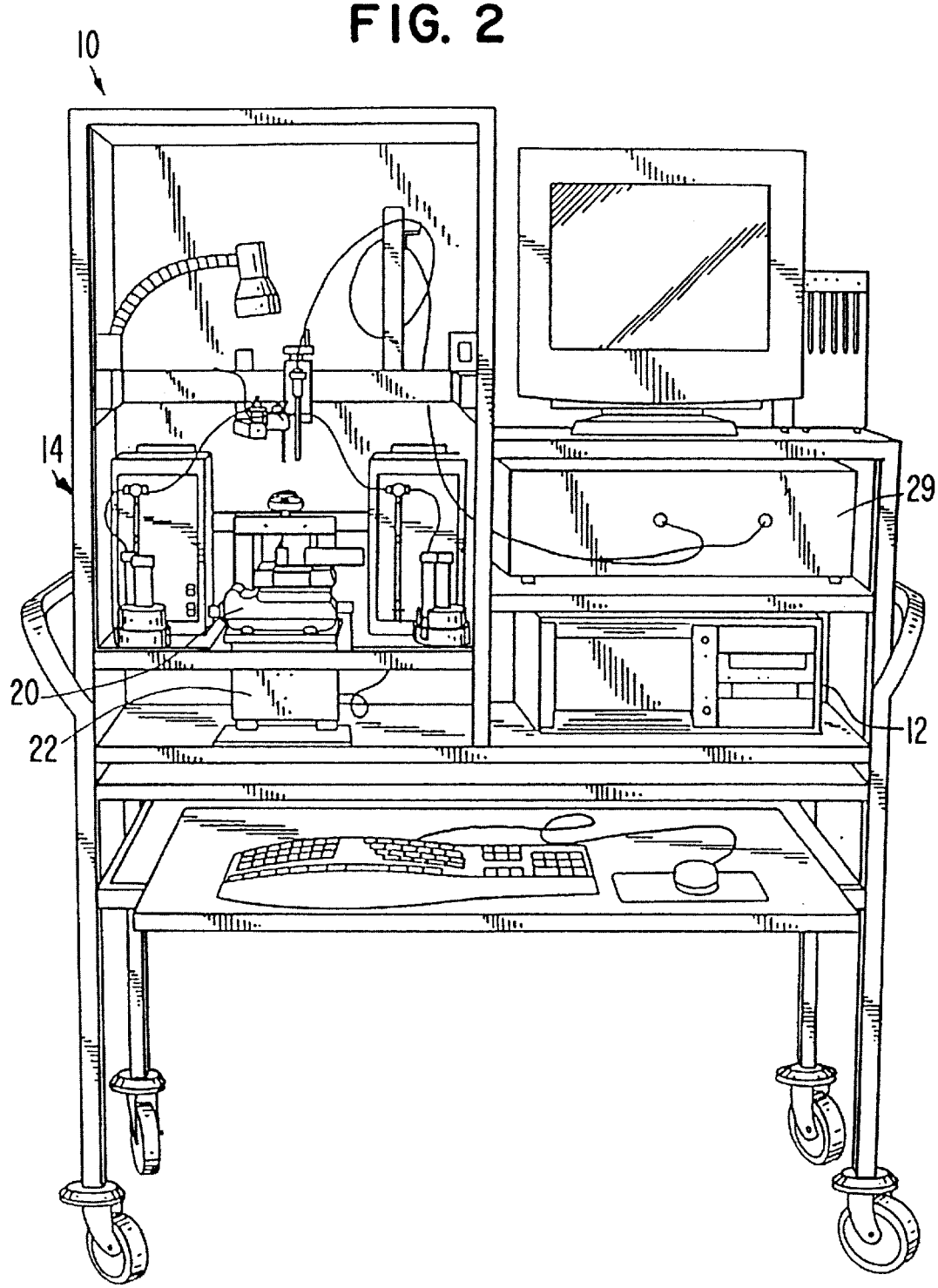
FIG. 2 is an elevational view of a preferred embodiment of an automated DNA compaction device showing the support, dispersion, dispensing, agitation, monitoring and control systems.

The automated compaction device of a preferred embodiment comprises components related to one another in a closed loop system, FIG. 1. The main components of compaction device 10 are control system 12; support and agitation system 14; measuring system 16 and dispensing system 18. As can be seen from the block diagram, the measuring system feeds back data about a batch solution to the control system which in turn commands the dispensing system and the agitation system. An iterative dispensing, measuring, analyzing operation is conducted on a batch solution of DNA or polycations by the control system until a desired composition is reached. At that point, the various components stop their functions so that the resulting compacted DNA particles can be removed. The components of the compaction device are preferably disposed together in movable fashion on a support and housing assembly as illustrated in FIG. 2. The details of the hardware components of the compaction device are described herein followed by an overview of the compaction method carried out by the compaction device and a detailed description of the operational protocol.

Figure 5:
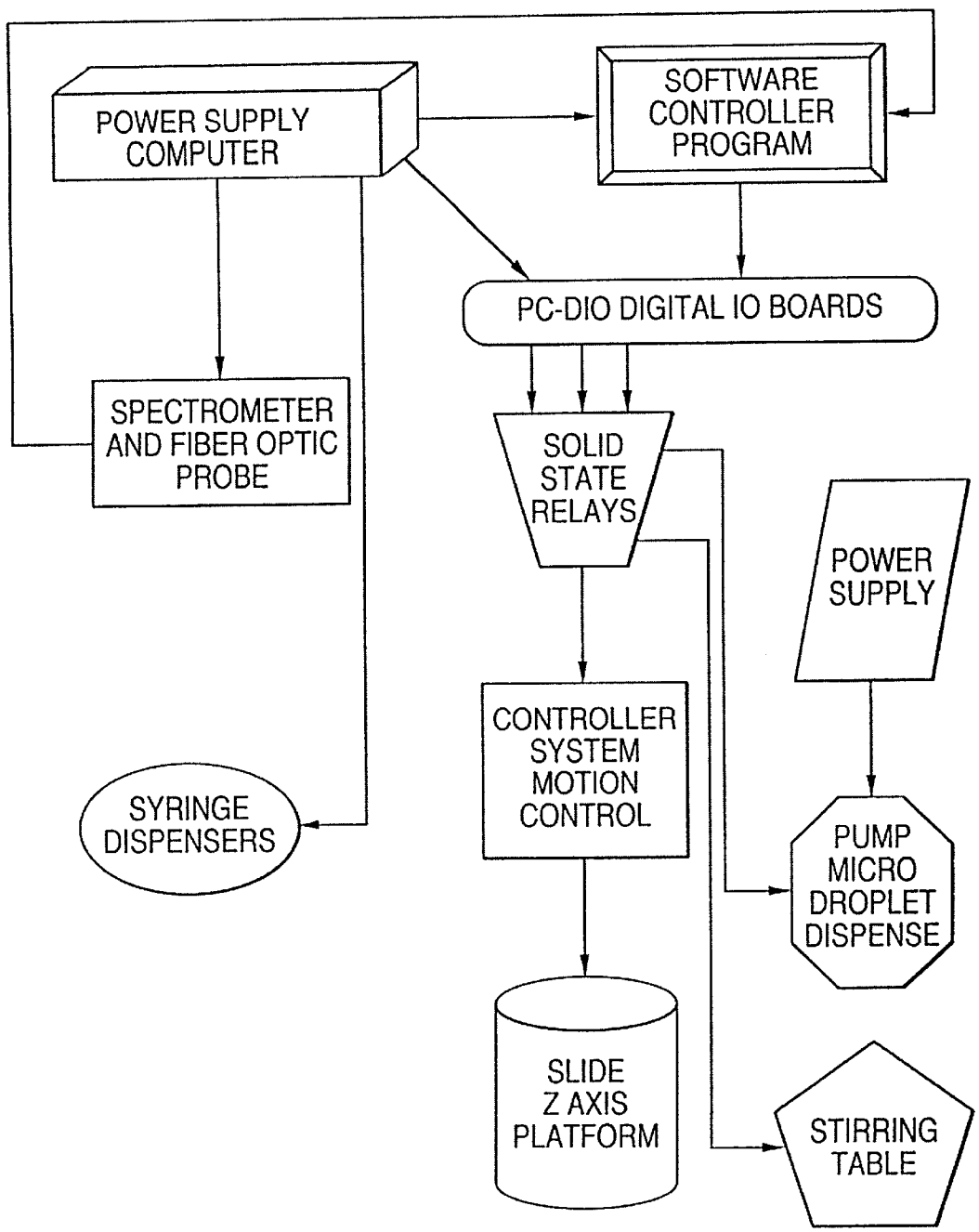
FIG. 5 is a schematic representation of the components of the compaction device of FIG. 2.

Control system 12 is broadly comprised of a computer equipped with an appropriate software program to control the functions of the other components and to analyze the data received by the measuring system. The control system also comprises appropriate digital input/output boards and connector boards that interface with the hardware elements of the compaction device (FIG. 5). The control system also comprises the normal input/output devices: a CRT monitor, keyboard and mouse as illustrated in FIG. 2. In the preferred embodiment, the control system comprises a Gateway 2000 PC with a Windows 95 operating system running a custom software controller program called Lab VIEW.

Support and agitation system 14 comprises a magnetic stirring table 20 mounted on a vertical slide support 22. Stirring table 20 comprises a platform jig which is adapted to support a beaker containing the batch solution. Magnetic stirring table 20 is movable along vertical slide so that a probe of the measuring system can be inserted into the beaker and dispensers of the dispensing system are able to dispense directly into the beaker. In a larger scale device, the probe could be configured to be movable if the platform is not movable vertically to mix the solution.

Figure 3:
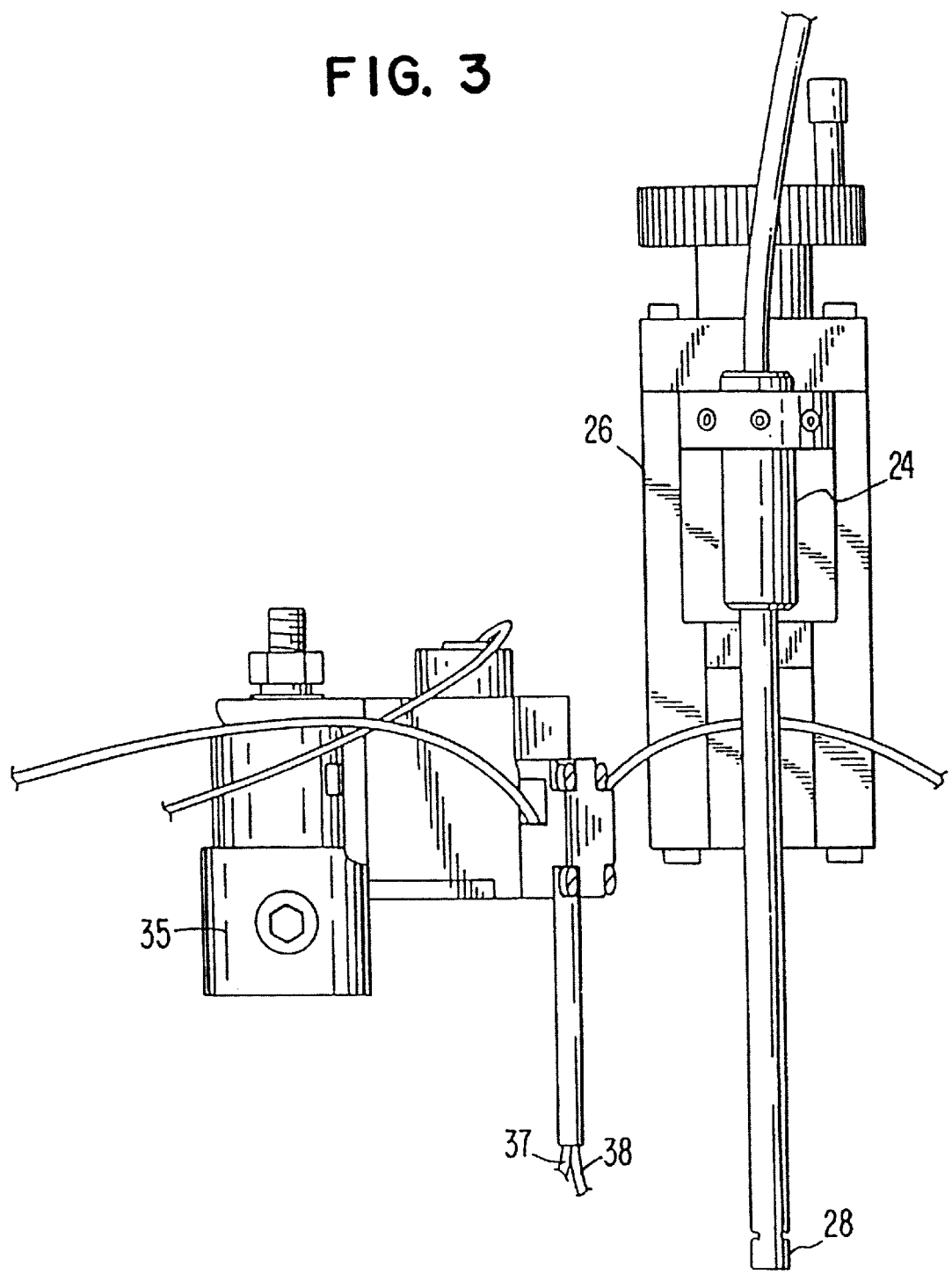
FIG. 3 is a detailed elevational view of the dispersion and dispensing systems and monitoring probe of the compaction device of FIG. 2.

Measuring system 16 comprises a probe 24, FIG. 3, which is capable of measuring some property or characteristic of the batch solution and providing such measurement to the control system for analysis. The property or characteristic chosen for measurement must be one that can be quantified for comparison and analysis by the control system. Properties such as particle size, concentration, or absorbance spectrum can be quantified and input to a control system for analysis. Other properties can also be used for measurement purposes. In the preferred embodiment, the probe is a fiber optic probe 24 mounted on a vertical slide support 26. Probe 24 is adapted to be inserted into the batch solution by movement along vertical slide support 26 until the point of the light path 28 of its tube is within the batch solution. Operationally, probe 24 is connected to a spectrometer 29 which provides a spectra reading to the control system for analysis. In the preferred embodiment a Zeiss MCS501 UV-Vis spectrometer is connected to a Zeiss GPIB transputer board which enables communication between the spectrometer and the control system. The transputer board employs programs in the Zeiss MCS 500 Labview library for operation of the spectrometer and to set the parameters for same.

Besides absorbance measurement, fluorescence, light scattering, zeta potential, circular dichroism and other known methods may be used for measurement and monitoring purposes with their attendant instruments coupled to the transputer board. The control system can be configured for monitoring the appropriate measured properties.

Figure 4:
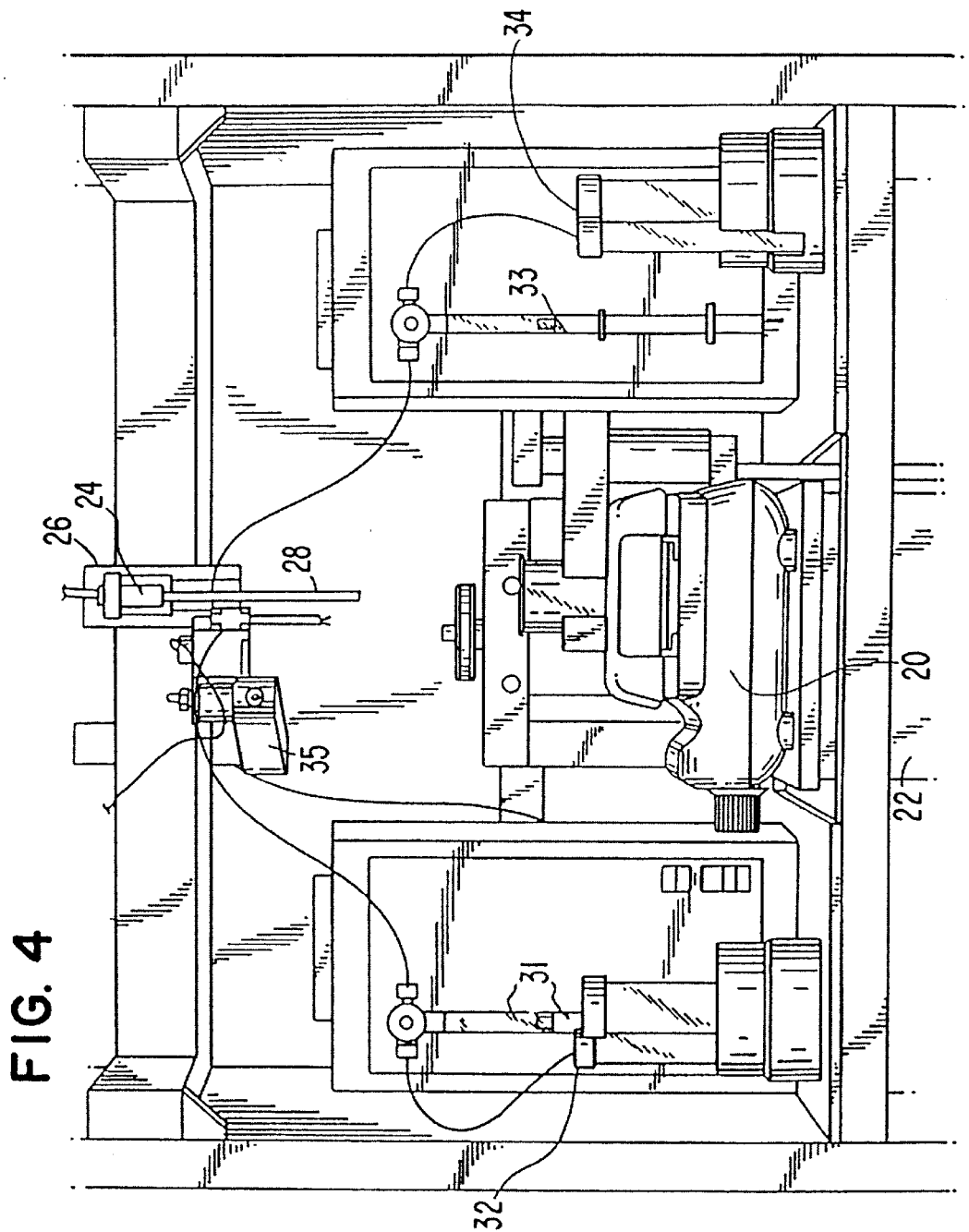
FIG. 4 is a detailed elevational view of the dispensing components of the support, dispersion, dispensing, agitation and monitoring systems of the compaction device of FIG. 2.

The dispensing system comprises a pair of microliter dispensing syringes 31, 33, FIG. 4, actuated by stepper motors 32, 34 operated by the control system, and a dispersion system. During operation of the compaction device, the dispensing syringes deliver their respective solutions into the beaker containing the batch solution as commanded by the control systems. The dispensers and motor can be programmed as to the speed in time per full stroke and volume per stroke.

In general, when dispensing micro-liter quantities, surface tension or capillary attraction forces prevent a micro-liter of solution from leaving the tip of the syringe. To overcome those forces and to ensure that the desired amount of additive solution leaves the syringe tip, the dispensing system comprises a sub-system for dispersing the additive solution into the batch solution. The dispersion system comprises a dispersion device 35 such as a sonicator or vibrator or aerosolizer. The dispersion device provides vibratory or oscillatory motion to dispensing tubing 37 and 38. Tubing 37 and 38 are connected to a variable resistor to oscillate the tubing at different frequencies during dispensing. This oscillation along with the mixing of the batch solution helps overcome any surface tension or capillary attraction forces, and allows for accurate dispensing of micro-liter quantities of additive solution into the batch solution.

In this preferred embodiment, the stepper motors are two Hamilton 511C dispensers which are connected to a serial communication port of the computer. These dispensers alternate delivery to the batch solution as commanded by the control system. During initialization of the compaction device the dispensers must be primed to fill the syringes and tubing and ensure the absence of air bubbles and leaks. This priming operation is done manually before the compaction device is actuated.

The compaction method carried out by the compaction device of the present invention begins with the gathering of reference data. After initialization of the device, a beaker of water is placed on the platform, the probe is immersed in the water and the stirring table actuated. The spectrometer measures a reference spectrum which is used as a baseline for all the absorbance spectra measured during the compaction operation. The reference spectrum is stored by the control system in a data log file.

After collection of the reference spectrum, the stirring is stopped and the vertical slide support lowers the platform so the beaker of water can be removed. A beaker containing a batch solution of nucleic acid or polycation is placed on the platform and affixed with the jig. The vertical slide raises the platform so that the probe is immersed in the batch solution and the stirring table actuated. Once the batch solution is in place, the delivery of the additive solutions and measurement of spectral data occur with feedback from the measuring system to the control system, and the control system commands the dispensing system. Default tolerance parameters are provided, but an operator may set desired tolerance parameters before the dispensing and measuring operations occur.

In a preferred embodiment, syringe dispenser 32 contains an additive solution referred to as additive solution A, and syringe dispenser 34 contains an additive solution referred to as additive solution B. Broadly, solution A is a polycation and solution B is a salt. Specifics of these solutions are described in the applications identified above. With the beaker containing the batch solution of nucleic acid in place, a predetermined amount of solution A is delivered to the batch solution in step-wise fashion. After a number of delivery steps, x, of solution A, an absorbance spectra is taken by the measuring system, and the data appended to the data log file. Delivery of solution A continues with absorbance spectra taken every x steps. The data of these absorbance spectra are appended to the data file.

After delivery of solution A is complete, a predetermined amount of solution B is delivered to the batch solution in step-wise fashion. After a number of delivery steps, x', of solution B, an absorbance spectra is taken by the measuring system, and the data appended to the data log file. Delivery of solution B continues with absorbance spectra taken every x' steps. The data of these additional absorbance spectra are appended to the data file.

The control system uses a predetermined formula to analyze the measured spectrum after each step delivery of solution B. The formula is used iteratively and when the returned value has not reached a predetermined threshold, the control system automatically commands one more dispensing cycle of solution B. Once the threshold value is reached, the control system commands the dispensing system to cease, the stirring table to cease, and the vertical slide support to lower the platform so the batch solution can be removed.

Figure 6:
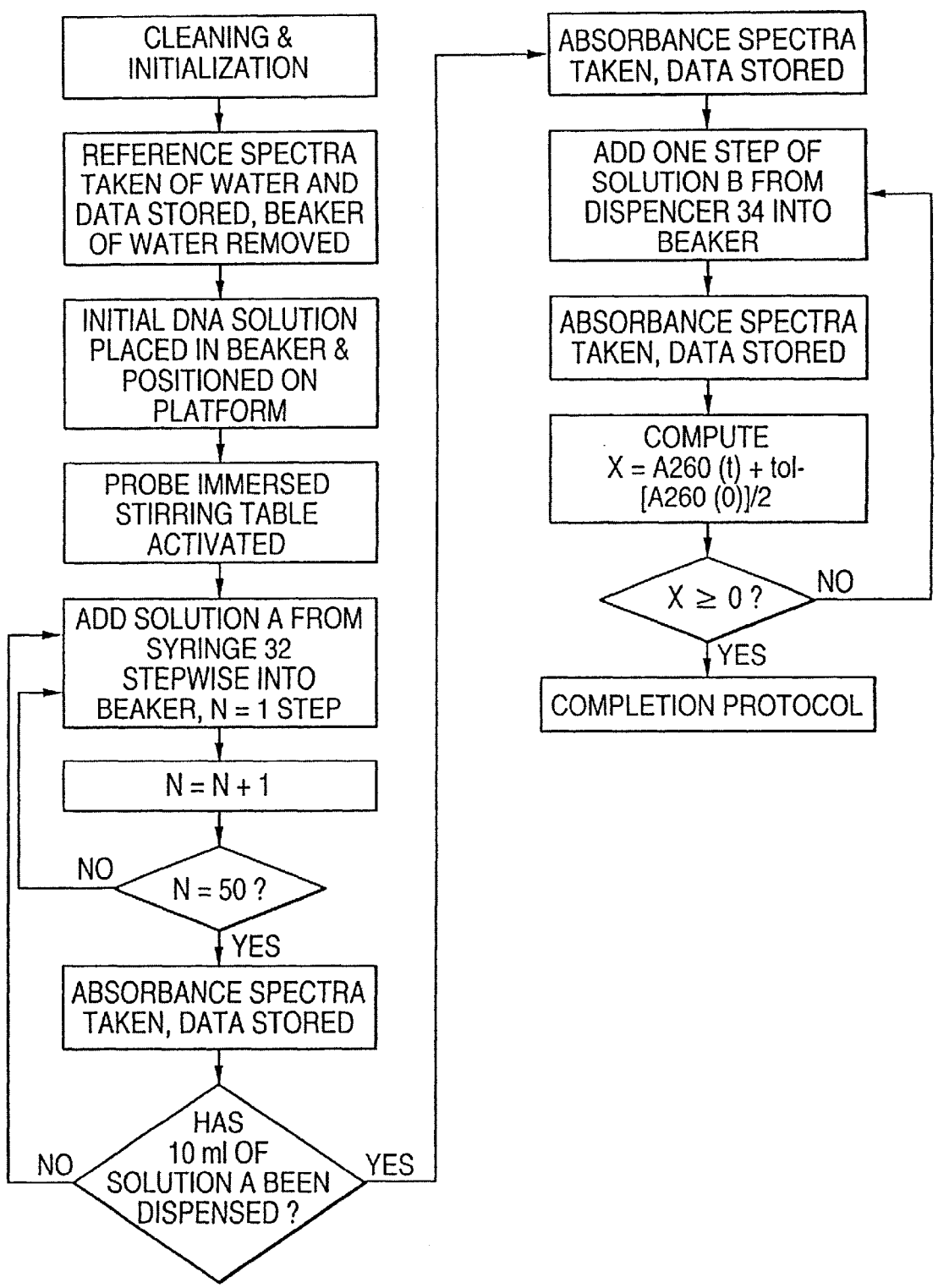
FIG. 6 is a flow diagram of an iterative compaction method of the automated compaction device.

As an example, the operation of a preferred embodiment of the compaction device is provided hereinbelow describing the settings, timing and volumes of the various solutions used in having the automated compaction device of the present invention perform the laboratory compaction method described in the Perales et al. article. A portion of the process is illustrated in the flow diagram of FIG. 6. This is directed to the compaction of DNA-galactosylated poly-L-lysine complexes for receptor-mediated endocytosis into cells in vitro and in vivo. A batch solution of 10 ml of DNA at a concentration of 0.2 to 1.0 mg/ml was placed in a beaker. The first syringe dispenser with 5 mL capacity is filled with solution A, 0.05 to 0.25 mg/ml galactosylated poly-L-lysine. One dispensing step or stroke of the first syringe corresponds to a 2.38 $\mu$L volume of solution A. The second syringe dispenser has a 4 mL capacity and was filled with solution B, a salt, in this example 5 molar NaCl. One dispensing step or stroke of the second syringe corresponds to a 1.19 μL volume of solution B. This compaction used a high salt formulation for solution B.

Once the batch solution was in place on the platform, the stirring table was actuated. The control system dispensed solution A in a step-by-step manner until 50 steps were delivered. The control system collected absorbance spectra, calculated data and appended the data to the log file. Dispensing continued until 1400 steps were delivered which corresponds to approximately 3.3 mL of solution A from the first dispenser. Due to the capacity of the dispenser, the control system instructs the dispenser to refill the syringe with liquid via a refilling tube. After refilling, delivery of solution A continued in a step-wise manner with spectra taken every 50 steps. There were a total of two refill operations during delivery of solution A. When 4200 steps were delivered, delivery of solution A was complete.

Then, into the beaker that contains the batch DNA solution and additive solution A, additive solution B was dispensed one step at a time. An absorbance spectrum was taken after the addition of every step of solution B, and the data were stored in the log file. The control system calculated θ as follows:

$$\theta = A_{260}(t) + tol - [A_{260}(0)]/2$$

where tol is the tolerance parameter (with a default value of 0.0001), and $A_{260}(0)$ is the spectrum at time=0, and $A_{260}(t)$ is the spectrum at time=t. If θ<zero, the control system commanded delivery of another step of solution B to the batch solution. This iterative delivery of solution B, absorbance spectrum measurement, and calculation and comparison continued until $\theta \geq 0$, the threshold level. At that point stop conditions to stop the addition of solution B were met, and the control system initiated the completion protocol. The completion protocol includes stopping the dispensers, stopping the stirring table, lowering the platform on the vertical slide support, stopping spectra analysis and recording data into a file in the computer.

The rates of dispensing are as follows: additive solution A is dispensed at a rate of 2.38 μL per 10 seconds, and additive solution B is dispensed at a rate of 1.19 μL per 10 seconds.

After this compaction operation, the resulting compacted DNA was compacted to a linear dimension that was greater than 100 times smaller than the DNA in the initial batch solution.

In an embodiment in which two additive solutions are used, solution B could also consist of a salt and/or an excipient. An excipient permits an increased concentration of compacted DNA to remain soluble, i.e., maintaining the DNA in physiological saline without precipitating. Solution B could consist of any compound which would stabilize the batch solution. While a salt, a salt plus an excipient or an excipient alone have been found to be useful for stabilizing the batch solution, other compounds could be effective as well.

It is also possible to formulate compacted DNA particles starting with an initial batch solution of nucleic acid and only one additive solution of polycations.

In another preferred embodiment in which only one additive solution is used, the initial batch solution consists of one or more polycations and syringe dispensers 31 or 33 contain an additive solution of DNA. With the beaker containing the batch solution of polycations in place, a predetermined amount of DNA is delivered to the batch solution in step-wise fashion. After a number of delivery steps, x, of DNA, an absorbance spectra is taken by the measuring system, and the data appended to the data log file. Delivery of DNA continues with absorbance spectra taken every x steps. The data of these additional absorbance spectra are appended to the data file.

While stepped dispensing is used in these preferred embodiments, it is well within the scope of the present invention to use other constant or variable flow rate dispensing methods. A different dispensing method may be especially advantageous if a predetermined formulation is employed instead of carrying out a monitored operation controlled by analysis of feedback data.

The compaction device, and the control system in particular, may be designed to allow an operator to intercede at any point during the process to carry out the remaining steps manually or to adjust any component. The spectrum measurement and analysis of the data can be actuated manually so that the measurement and calculation functions are still performed by the control system, but the control system cedes automatic control of the process to an operator.

Before a compaction process is carried out, the compaction device must be initialized. The primary requirements of initialization are to ensure that the dispensing system is clean and that there would be no expected interruptions to the experiment once begun. All of the computer components such as the CPU, digital input/output board, spectrometer and transputer board go through standard initialization and diagnostic processes. All of the channels of the board are set to 0V when the computer is powered up and initialized. Among the manual initialization steps is the priming of the dispensers with solutions A and B. The computer will prompt an operator to prime the dispensers and will wait for operator input as to completion of this task before proceeding. The control system refills the syringe with solution A and starts dispensing solution A one step at a time until the operator inputs a stop command. The syringe of the second dispenser is then primed with solution B which is also dispensed one step at a time until the operator inputs a stop command. In this manner the syringes are filled with solutions A and B and the operator examines the system to ensure that no air bubbles or leaks are present. Any drops of solution remaining on the tips of the syringes are cleaned off After initialization, the operator would be instructed by the control system via the CRT to place a beaker containing deionized water on the platform. When the beaker containing water is in place, the operator commands the compaction device to proceed. The control system sends a pulse to the vertical slide support control which raises the platform to a height appropriate for immersion of the probe into the water. The stirring table is actuated to stir the water in the beaker and a probe is immersed while the water is being stirred. A reference spectrum is taken and the data saved in a log file as described above.

While the following examples are directed to the compaction of DNA, it is to be understood that claimed device and method also compact other types of nucleic acid as disclosed in U.S. Pat. Nos. 5,844,107 and 5,877,302, and such compaction is deemed to be within the scope of the claimed invention.

The control system could also operate a compaction routine which is based on a predetermined formulation of amounts of solution and rates of addition, without use of any feedback data. Of course the control system may collect such data for monitoring purposes when a predetermined formulation is run.

From the foregoing detailed description, it will be evident that there are a number of changes, adaptations, and modifications of the present invention which come within the province of those skilled in the art. However, it is intended that all such variations not departing from the spirit of the invention be considered as within the scope thereof as limited only by the claims appended hereto.

EXAMPLE 1

In this example, DNA is compacted in the absence of chaotropic salt. A batch solution consists of 10 ml of DNA at a concentration of 0.1 mg/ml (0.30 μmol negative charges/ml), and the additive solution A consists of CK8 polycation at a concentration of 0.08 mg/ml (0.33 μmole positive charges/ml); the diluent for both solutions is highly purified, HPLC-grade water. The first syringe dispenser has a 5 ml capacity and is loaded with polycation. One dispensing step or stroke of the first syringe corresponds to a 2.38 μL volume of CK8. Once the batch solution is in place on the platform and the stirring table is actuated, the control system dispenses solution A in a step-by-step manner until 50 steps are delivered. The control system collects absorbance spectra, calculates data and appends the data to the log file. Dispensing continues until 1400 steps are delivered which corresponds to approximately 3.3 ml of DNA from the first dispenser. Due to the capacity of the dispenser, the control system instructs the dispenser to refill the syringe with liquid via a refilling tube. After refilling, delivery of solution A continues in a step-wise manner with spectra taken every 50 steps. There are a total of two refill operations during the delivery of DNA in this particular example. After addition of 7 ml of solution A, the dispenser is stopped manually; the ratio of positive to negative charges mixed in the chamber is approximately 0.77.

Figure 7:
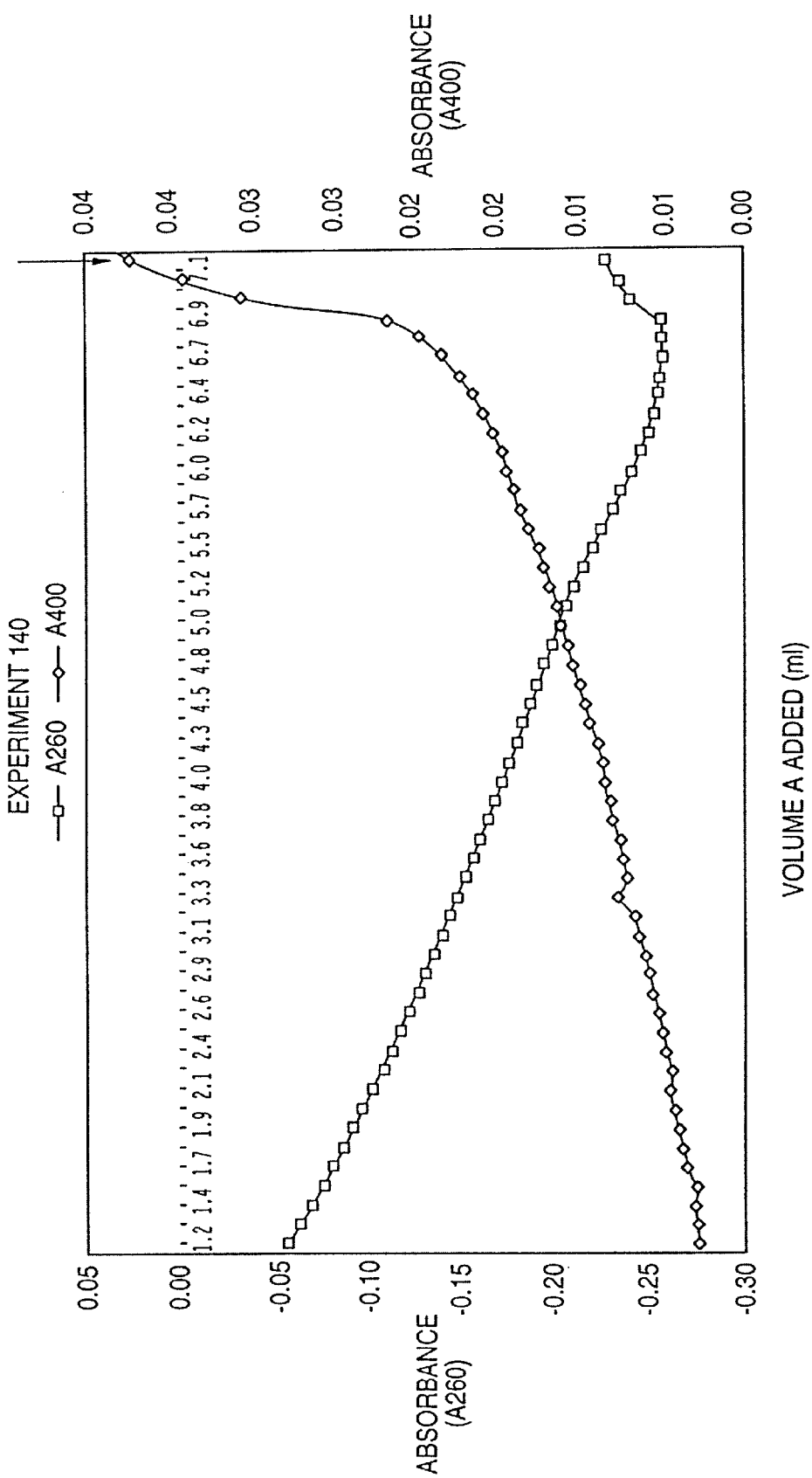
FIG. 7 is a plot of spectral probe data observed during automated preparation of compacted DNA using parameters outlined in Example 1.
Figure 8:
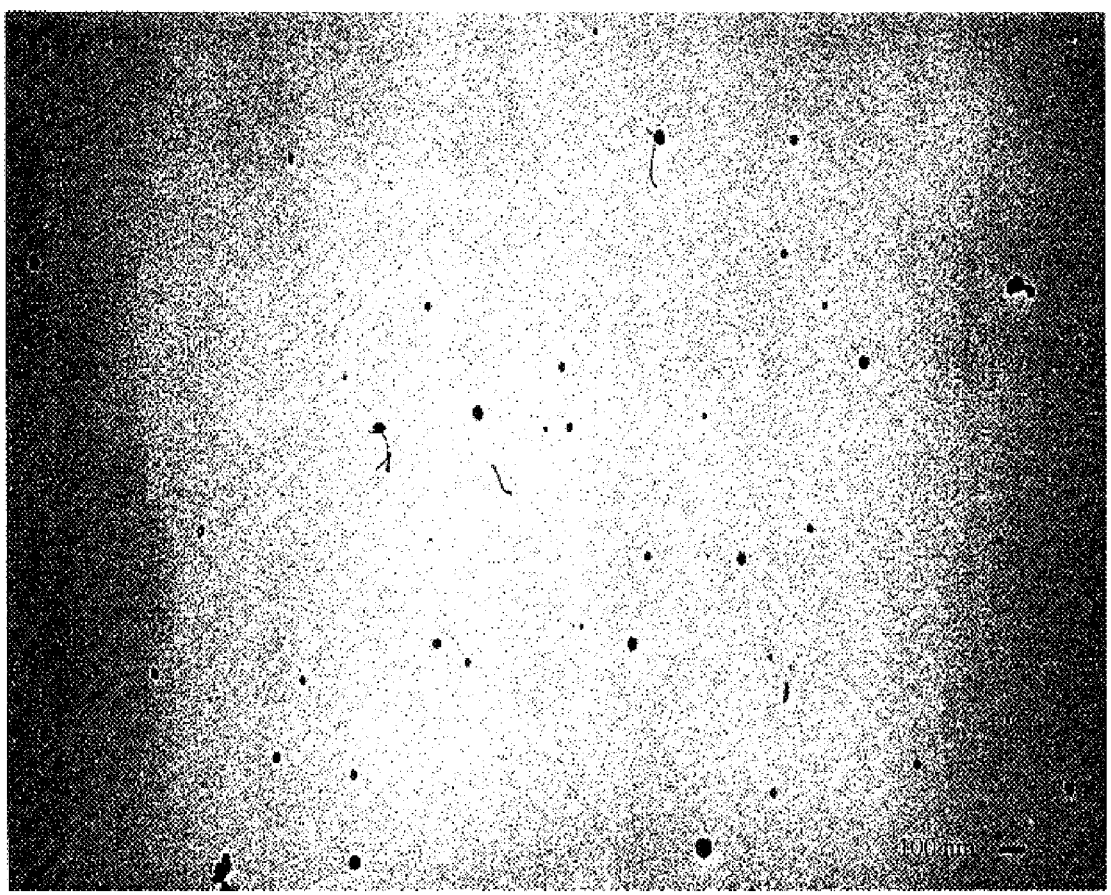
FIG. 8 is an electron micrograph of automated preparation of compacted DNA using the formulation method of Example 1.

FIG. 7 presents the spectral probe data observed during automated preparation of compacted DNA using parameters outlined this example. $A_{260}$ (left axis) monitors approximate DNA concentration (value partially dependent on DNA conformation and state of aggregation) and $A_{400}$ (right axis) monitors light scattering by compacted DNA particles. The arrow in FIG. 7 denotes when a sample of the batch solution was analyzed for compacted DNA using electron microscopy as seen in FIG. 8. Electron dense particles of compacted DNA have a diameter of approximately 29 nm, with some larger particles also observed. The bar scale in the FIG. 8 measures 100 nm.

EXAMPLE 2

In this example, a batch solution consists of polycation and the additive solution consists of DNA. In preferred embodiments, the charge ratio of positively charged peptide to negatively charged DNA phosphate groups ranges from 1:1 to 2:1 to 4:1 to 10:1 to 20:1 to 50:1. The exact ratio of positive to negative charges depends on the relative volumes of DNA and polycation, the relative rates of addition, the rate of solution mixing, temperature, pH, and a variety of other parameters, including ionic strength and salt composition of the DNA and polycation. The rate of addition of DNA to polycation is chosen so as to prevent aggregation and/or precipitation of the DNA. The maximum concentration of soluble, compacted DNA in the compaction chamber is dependent upon a number of factors, including the exact specification of the polycation, use of potential targeting moieties that are covalently attached to the polycation, and use of excipients either during or after completion of the compaction process.

In the compaction run analyzed in FIGS. 9–12, the initial batch solution consists of 2.4 ml of CK30 polymer at a concentration of 2.25 mg/ml in water (9.3 μmol/ml positive charges), and solution A consists of DNA at a concentration of 0.32 mg/ml in water (0.97 μmol/ml negative charges). The first syringe dispenser has a 5 ml capacity and is loaded with DNA. One dispensing step or stroke of the first syringe corresponds to a 2.38 μL volume of DNA.

Once the batch solution is in place on the platform and the stirring table is actuated, the control system dispenses solution A in a step-by-step manner until 50 steps are delivered. The control system collects absorbance spectra, calculates data and appends the data to the log file. Dispensing continues until 1400 steps are delivered which corresponds to approximately 3.3 ml of DNA from the first dispenser. Due to the capacity of the dispenser, the control system instructs the dispenser to refill the syringe with liquid via a refilling tube. After refilling, delivery of solution A continues in a step-wise manner with spectra taken every 50 steps. There are a total of two refill operations during the delivery of DNA in this particular example. A total of 10 ml of solution A (DNA) are added to the batch solution.

Figure 9:
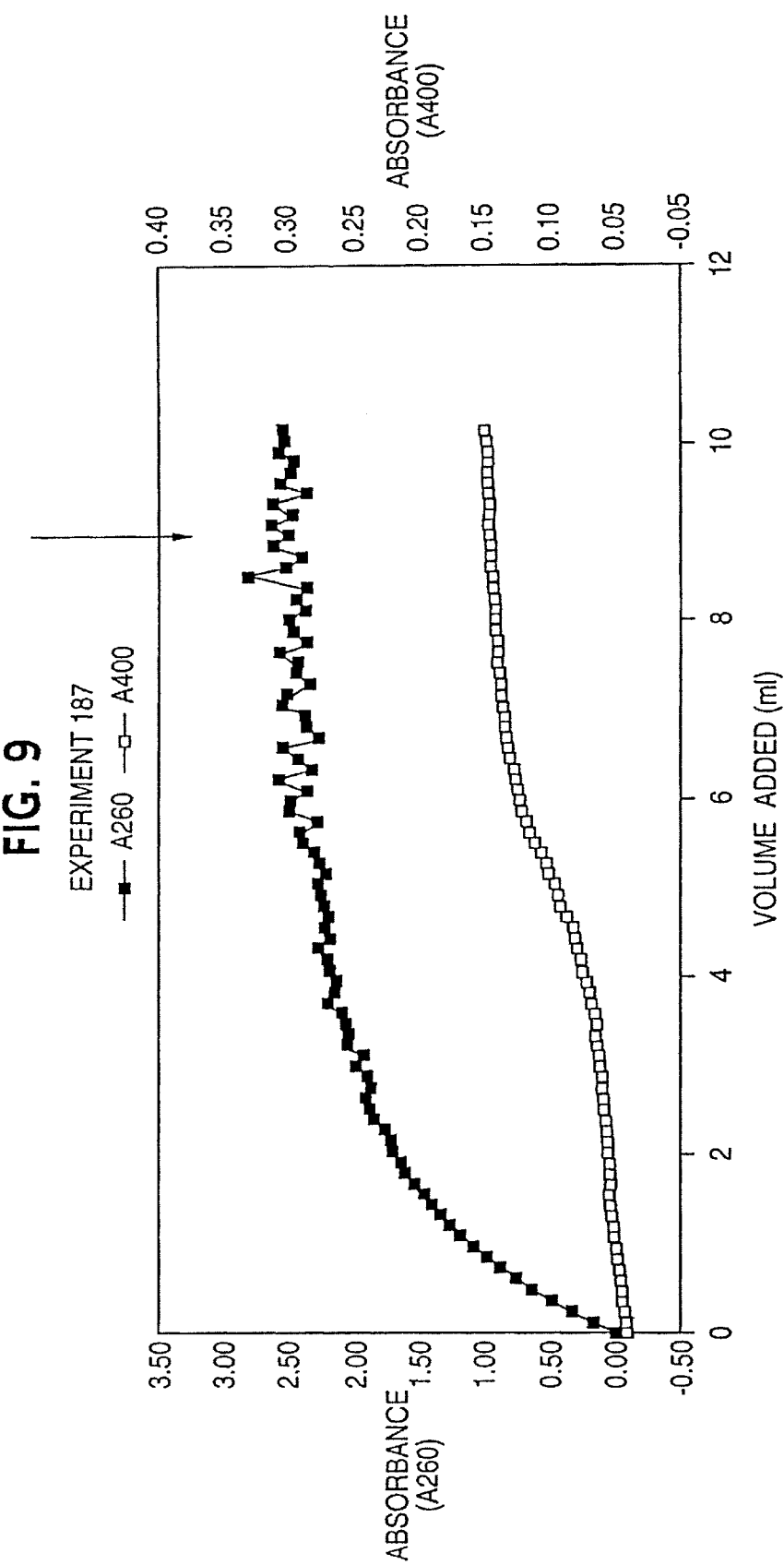
FIG. 9 is a plot of spectral probe data observed during automated preparation of compacted DNA using parameters outlined in Example 2.

FIG. 9 presents spectral probe data collected during the compaction run. $A_{260}$ (left axis) monitors approximate DNA concentration (value partially dependent on DNA conformation and state of aggregation) and $A_{400}$ (right axis) monitors light scattering by compacted DNA particles. Note that the $A_{260}$ profile is essentially predicted by the dilution of DNA during the compaction run, and the light scattering profile shows a roughly proportional increase during the titration. The formulation method of Example 2 results in unimolecularly compacted and unaggregated DNA particles in direct proportion to the amount of added DNA; states of relative aggregation and disaggregation of unimolecularly compacted DNA are not evident by either spectral probe measurements or by serial electron micrographs. The arrow in FIG. 9 denotes when a sample of the batch solution was analyzed for compacted DNA using electron microscopy and dynamic light scattering as seen in FIGS. 10 and 11.

Figure 10:
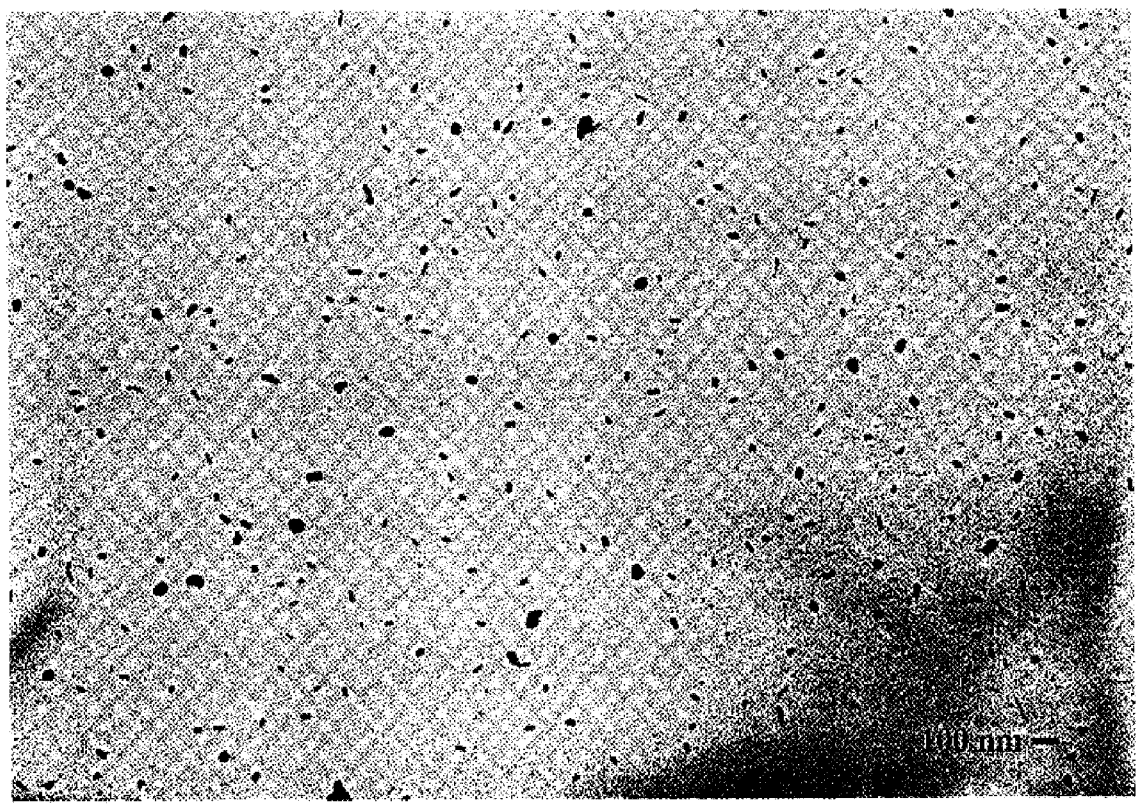
FIG. 10 is an electron micrograph of automated preparation of compacted DNA using the formulation method of Example 2.

FIG. 10 shows an electron micrograph of compacted DNA. Note that a majority of the DNA complexes have a diameter of approximately 20–25 nm; some larger complexes are also observed. The bar scale in the photograph measures 100 nm. Agarose electrophoresis of this preparation indicates that essentially all of the DNA was compacted; no free DNA was observed (data not shown).

Figure 11:
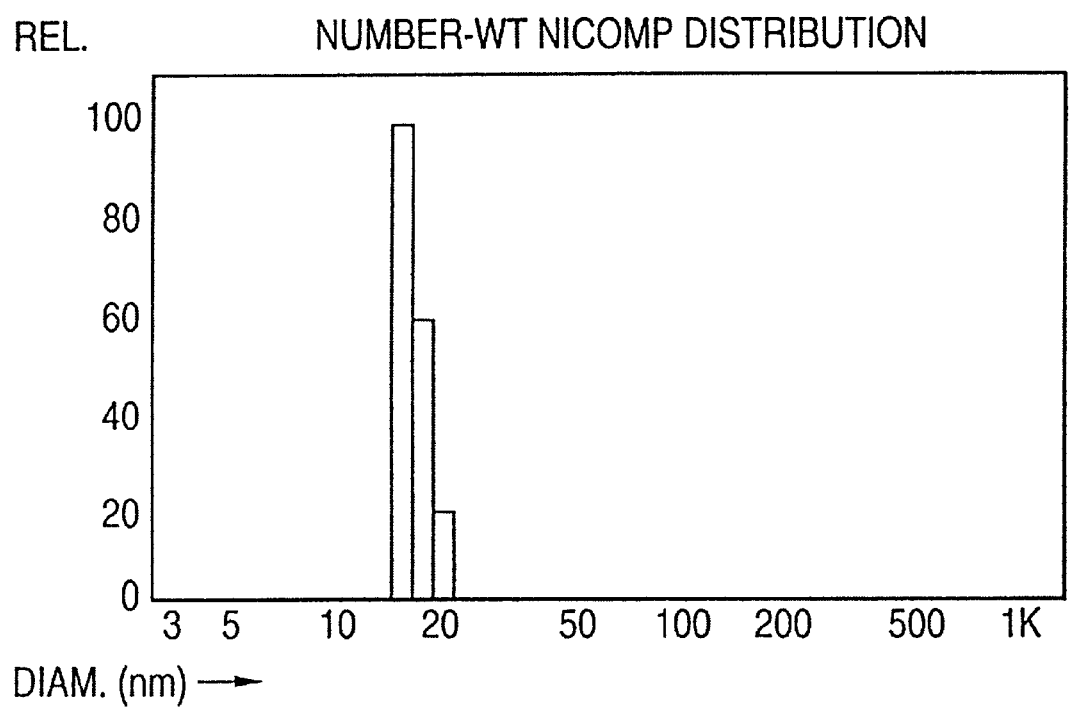
FIG. 11 is a dynamic light scattering profile of automated preparation of compacted DNA using the formulation method of Example 2.

FIG. 11 shows a dynamic light scattering analysis of the same DNA sample. The DNA sample was evaluated using a Particle Sizing Systems dynamic light scattering instrument. The data fit a bimodal Nicomp distribution and have a fit error of 1.541. The predominant peak (99.2% in the numerical weighted histogram) has a mean size of 17.3 nm. A minor peak comprising 0.8% of the signal has a mean size of 75.5 nm. Hence, there is a good correlation between the sizes measured using either electron microscopy or dynamic light scattering. Table 1 contains the summary corresponding to FIG. 11.

TABLE 1

NUMBER-Weighted NICOMP DISTRIBUTION Analysis (Solid Particle)

NICOMP SUMMARY

Peak #1: Mean Diam. = 17.3 nm, S. Dev. = 21.8 nm (125.6%)
Num = 99.2%
Peak #2: Mean Diam. = 75.5 nm, S. Dev. 12.1 nm (16.1%) Num = 0.8%
Mean Diameter = 17.7 nm     Fit Error = 1.541     Residual = 6.806

TABLE 1-continued

NUMBER-Weighted NICOMP DISTRIBUTION Analysis (Solid Particle)

NICOMP SCALE PARAMETERS:

| | |
|---|---|
| Min. Diam. = 3 nm | Plot Size = 42 |
| Smoothing = 3 | Plot Range = 500 |

In this example, a feedback mechanism to control addition of DNA to polycation is not necessarily needed since states of aggregation and disaggregation of unimolecularly compacted DNA are not observed. However, formulations which employ other compositions and/or concentrations of DNA and polycation may be optimized by use of a controlling system to provide control to the dispensers based on input data from the monitoring system.

Figure 12:
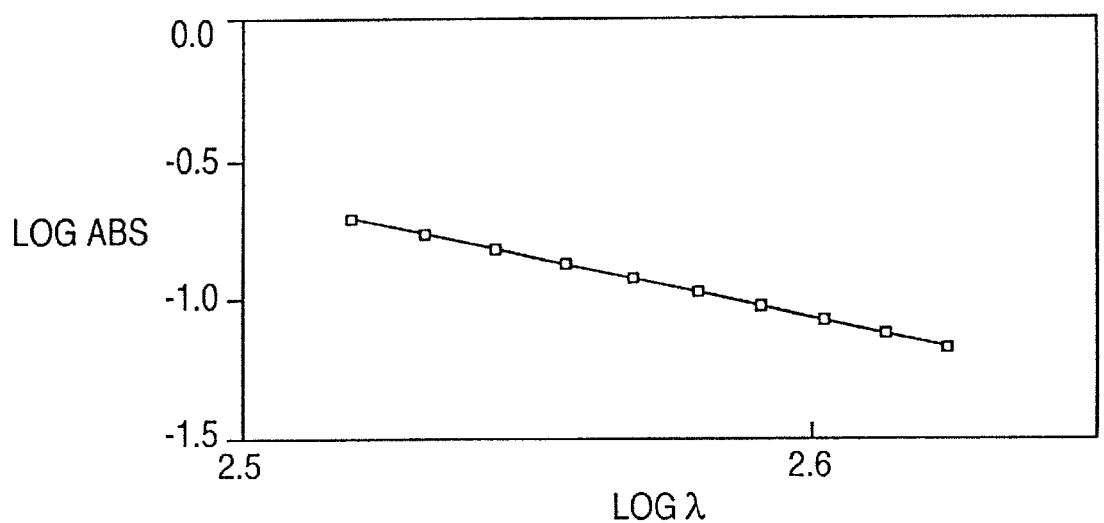
FIG. 12 is a log absorbance versus log wavelength plot of the turbidity parameter analysis of compacted DNA using the formulation method of Example 2.

Appropriately prepared, compacted DNA complexes are soluble and unaggregated in solution, and are predicted to scatter light according to Rayleigh's law. This theorem predicts that particles having a diameter significantly smaller than the wavelength of the incident light will scatter light in inverse proportion to the $4^{th}$ power of the wavelength. The DNA complexes prepared in this example were evaluated for optical density at incident wavelengths between 330–420 nm. In this range, there is no absorbance of light due to specific bonds in either DNA or polylysine; rather, the observed absorbance values are entirely due to scattering of light by the compacted DNA particles. As shown in FIG. 12, a plot of log absorbance versus log incident light wavelength gives a straight line with a slope of −4.42+/−0.037 (SE). The turbidity parameter is defined as the slope of this plot. Table 2 contains the data corresponding to FIG. 12.

TABLE 2

| Variables | |
|---|---|
| Slope | −4.421 ± 0.03732 |
| Y-intercept | 10.44 ± 0.09602 |
| X-intercept | 2.361 |
| 1/slope | −0.2262 |
| 95% Confidence Intervals | |
| Slope | −4.507 to −4.334 |
| Y-intercept | 10.21 to 10.66 |
| Goodness of Fit | |
| $r^2$ | 0.9994 |
| Sy.x | 0.003942 |
| Is slope significantly non-zero? | |
| F | 14030 |
| DFn, DFd | 1.000, 8.000 |
| P value | <0.0001 |
| Deviation from zero? | Significant |
| Data | |
| Number of X values | 10 |
| Maximum number of Y replicates | 1 |
| Total number of values | 10 |
| Number of missing values | 0 |

In other experiments, the average turbidity parameter value for 42 unique compaction formulations using the compaction device was −4.13+/−0.24 (SD). These results demonstrate that compacted DNA complexes scatter light in accordance with theoretical predictions as presented in Rayleigh's law. It has been observed that preparations of compacted DNA that aggregate (because of specific solvent effects) scatter light with a smaller slope value, typically in the range of −3.0 to −3.4. In one embodiment of the compaction device, this turbidity plot analysis is performed real-time during the actual process of compacting DNA. This analysis permits quality control of compacted DNA during the entire formulation process.

What is claimed is:

1. A device for compacting nucleic acid complexes to a desired state or size, said device comprising:

a support for supporting a batch solution;

a dispenser for dispensing an additive solution to the batch solution, the additive solution or the batch solution containing the nucleic acid, and after addition of the additive solution the batch solution contains nucleic acid complexes;

a monitor coupled to a submersible probe and a measurement apparatus for monitoring the batch solution to determine whether nucleic acid complexes in the batch solution have reached the desired state or size, wherein said submersible probe is adapted to be placed in the batch solution, said measurement apparatus is connected to said probe for generating measurement data regarding the state or size of the nucleic acid complexes;

a processor coupled to said measurement apparatus whereby said processor receives measurement data and calculates whether the nucleic acid complexes have reached a threshold size; and a controller coupled to said processor and said dispenser to control dispensing of the additive solution in response to a signal from said processor.

2. The device of claim 1, wherein said monitor and said controller are operatively coupled in a feedback configuration.

3. The device of claim 1, wherein said support provides motion to the batch solution.

4. The device of claim 3, wherein the motion is a vortexing motion.

5. The device of claim 1, wherein said support comprises a magnetic stirring platform.

6. The device of claim 1, wherein said dispenser comprises a constant flow rate dispensing mechanism.

7. The device of claim 1, wherein said dispenser comprises a variable flow rate dispensing mechanism.

8. The device of claim 1, wherein said dispenser is adapted to dispense micro-liter quantities.

9. The device of claim 8, wherein said dispenser comprises a dispersion device to disperse micro-liter quantities of additive solution into batch solution.

10. The device of claim 1, wherein said dispenser comprises a plurality of dispensing elements.

11. The device of claim 1, wherein said measurement apparatus comprises a spectrometer for measuring absorption.

12. The device of claim 1, wherein said measurement apparatus comprises a spectrometer for measuring light scattering.

13. The device of claim 1, wherein said measurement apparatus comprises a spectrometer for measuring zeta potential.

14. The device of claim 1, wherein said measurement apparatus comprises a spectrometer for measuring circular dichroism.

15. The device of claim 1, wherein said measurement apparatus comprises a fluorimeter for measuring fluorescence.

16. The device of claim 3, wherein motion is provided to the batch solution when said dispenser dispenses the additive solution.

17. The device of claim 1, further comprising a batch solution of nucleic acid.

18. The device of claim 1, further comprising a batch solution of polycation.

19. A device for compacting nucleic acid complexes to a desired state or size, said device comprising:
   a batch solution receptacle;
   a dispensing system adapted to deliver an additive solution to the batch solution, the additive solution or the batch solution containing the nucleic acid, and after addition of the additive solution the batch solution contains nucleic acid complexes;
   a measurement apparatus for generating measurement data regarding the size of nucleic acid complexes in the batch solution;
   a processor coupled to said measurement apparatus whereby said processor receives measurement data and calculates whether the nucleic acid complexes have reached a predetermined threshold size; and
   a controller coupled to said processor and said dispensing system to regulate dispensing of the additive solution.

20. The device of claim 19, further comprising:
   a monitor coupled to said measurement apparatus for monitoring the state or size of the nucleic acid complex.

21. The device of claim 20, wherein said measurement apparatus comprises a submersible probe positionable in the batch solution receptacle.

22. The device of claim 20, wherein said measurement apparatus comprises a spectrometer for measuring absorption.

23. The device of claim 20, wherein said measurement apparatus comprises a spectrometer for measuring light scattering.

24. The device of claim 20, wherein said measurement apparatus comprises a spectrometer for measuring zeta potential.

25. The device of claim 20, wherein said measurement apparatus comprises a spectrometer for measuring circular dichroism.

26. The device of claim 20, wherein said measurement apparatus comprises a fluorimeter for measuring fluorescence.

27. The device of claim 20, wherein said measurement apparatus and said controller are operatively coupled in a feedback configuration.

28. The device of claim 19, wherein said batch solution receptacle provides mixing motion to the batch solution.

29. The device of claim 28, wherein the motion is a vortexing motion.

30. The device of claim 19, further comprising a magnetic stirring platform for supporting said batch solution receptacle.

31. The device of claim 30, wherein motion is provided to the batch solution when said dispensing system dispenses the additive solution.

32. The device of claim 19, wherein said dispensing system comprises a constant flow rate dispensing mechanism.

33. The device of claim 19, wherein said dispensing system comprises a variable flow rate dispensing mechanism.

34. The device of claim 19, wherein said dispensing system is adapted to dispense micro-liter quantities.

35. The device of claim 19, wherein said dispensing system comprises a dispersion device to disperse micro-liter quantities of additive solution into the batch solution.

36. The device of claim 19, wherein said dispensing system comprises a plurality of dispensers.

37. The device of claim 19, further comprising a batch solution of nucleic acid.

38. The device of claim 19, further comprising a batch solution of a polycation.

39. A nucleic acid compaction device for compacting nucleic acid to a desired state or size, said device comprising:
   an additive solution dispenser;
   a batch solution receptacle;
   a measurement apparatus adapted to monitor contents of said batch solution rceptacle and generate measurement data regarding the state or size of the nucleic acid complexes; and
   a processor coupled to said dispenser and said measurement system for analyzing the measurement data and determining whether the nucleic acid complexes have reached a desired state or size.

40. The nucleic acid compaction device of claim 39, further comprising a mixer operatively coupled with said batch solution receptacle and adapted to provide a mixing motion to a batch solution contained in said receptacle.

41. The nucleic acid compaction device of claim 40, wherein said mixer comprises a magnetic stirring platform supporting said batch solution receptacle.

42. The nucleic acid compaction device of claim 40, wherein said mixer comprises a dispersion device attached to said additive solution dispenser capable of dispersing an additive solution into a batch solution contained in said receptacle.

43. The nucleic acid compaction device of claim 39, further comprising a controller coupled to said dispenser adapted to regulate delivery of an additive solution to a batch solution.

44. The nucleic acid compaction device of claim 39, further comprising a monitor adapted to analyze the state or size of nucleic acid in a batch solution contained in said receptacle.

45. The nucleic acid compaction device of claim 43, further comprising a monitor adapted to analyze the state or size of nucleic acid in a batch solution contained in said receptacle.

46. The nucleic acid compaction device of claim 45, wherein said monitor is operatively coupled to said controller in a feedback configuration to regulate delivery of the additive solution depending on the state or size of nucleic acid in the batch solution and stop delivery of the additive solution when nucleic acid in the batch solution has reached the desired state or size.

47. A method of compacting nucleic acid to a desired state or size comprising the steps of:
   providing an automated nucleic acid compaction device including a measurement apparatus coupled to a processor to monitor a batch solution containing nucleic acid; and
   compacting nucleic acid to the desired state or size using the automated nucleic acid compaction device wherein the processor receives measurement data and calculates whether the nucleic acid complexes have reached a threshold state or vice.

48. The method of claim 47, wherein said method is repeatable to yield a given state or size of nucleic acid.

49. The method of claim 47, wherein said compacting step produces compacted, unimolecular nucleic acid particles.

50. The method of claim 47, wherein said compacting step produces compacted spherical nucleic acid particles smaller than 90 nm in diameter.

51. The method of claim 50, wherein said compacting step produces compacted spherical nucleic acid particles smaller than 50 nm in diameter.

52. The method of claim 51, wherein said compacting step produces compacted spherical nucleic acid particles smaller than 25 nm in diameter.

53. The method of claim 47, wherein said compacting step produces compacted cylindrical nucleic acid particles.

54. The method of claim 47, wherein said compacting step produces compacted nucleic acid particles of toroidal shape.

55. The method of claim 49, wherein said compacting step produces compacted spherical nucleic acid particles smaller than 90 nm in diameter.

56. The method of claim 55, wherein said compacting step produces compacted spherical nucleic acid particles smaller than 50 nm in diameter.

57. The method of claim 56, wherein said compacting step produces compacted spherical nucleic acid particles smaller than 25 nm in diameter.

58. The method of claim 49, wherein said compacting step produces compacted cylindrical nucleic acid particles.

59. The method of claim 49, wherein said compacting step produces compacted nucleic acid particles of toroidal shape.

* * * * *

UNITED STATES PATENT AND TRADEMARK OFFICE
CERTIFICATE OF CORRECTION

PATENT NO.    : 6,281,005 B1
DATED         : August 28, 2001
INVENTOR(S)   : Hector L. Casal et al.

It is certified that error appears in the above-identified patent and that said Letters Patent is hereby corrected as shown below:

Title page,
Item [74], *Attorney, Agent or Firm*, "BB" has been deleted

Column 14,
Line 60, "vice" has been replaced with -- size --

Signed and Sealed this

Second Day of July, 2002

*Attest:*

*Attesting Officer*

JAMES E. ROGAN
*Director of the United States Patent and Trademark Office*